(12) United States Patent
Bae et al.

(10) Patent No.: US 10,018,875 B2
(45) Date of Patent: Jul. 10, 2018

(54) CURVED LIQUID CRYSTAL DISPLAY AND METHOD OF MANUFACTURING THE SAME

(71) Applicant: Samsung Display Co. Ltd., Yongin, Gyeonggi-do (KR)

(72) Inventors: Ji Hong Bae, Yongin-si (KR); Heung Shik Park, Seoul (KR); Keun Chan Oh, Cheonan-si (KR)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 22 days.

(21) Appl. No.: 15/002,012

(22) Filed: Jan. 20, 2016

(65) Prior Publication Data

US 2017/0052412 A1    Feb. 23, 2017

(30) Foreign Application Priority Data

Aug. 18, 2015 (KR) .................. 10-2015-0115881

(51) Int. Cl.
*G02F 1/1337* (2006.01)
*G02F 1/1341* (2006.01)
(Continued)

(52) U.S. Cl.
CPC ...... *G02F 1/133711* (2013.01); *C07D 211/22* (2013.01); *C07D 211/46* (2013.01); *C08G 73/1042* (2013.01); *C08G 73/1078* (2013.01); *C09K 19/3483* (2013.01); *C09K 19/54* (2013.01); *C09K 19/542* (2013.01);
(Continued)

(58) Field of Classification Search
CPC ......... G02F 1/133788; G02F 1/133711; G02F 1/133723; G02F 1/133753; G02F 1/133707; G02F 1/1343; G02F 1/134309; G02F 1/133761; G02F 1/1337; G02F 1/1335; G02F 1/133514; G02F 1/1333; G02F 1/133305; G02F 1/136; G02F 1/1362; G02F 1/136227; G02F 1/13624; G02F 1/1368; G02F 2001/133742; G02F 2001/133726; G02F 2001/133757; C09K 19/02;
(Continued)

(56) References Cited

U.S. PATENT DOCUMENTS

2012/0212691 A1* 8/2012 Miyakawa ........ G02F 1/133788
349/86
2012/0249940 A1* 10/2012 Choi ................. G02F 1/133753
349/123

(Continued)

FOREIGN PATENT DOCUMENTS

EP         2463355        11/2011
JP       2003-215592   *  7/2003
(Continued)

*Primary Examiner* — Thoi Duong
(74) *Attorney, Agent, or Firm* — Cantor Colburn LLP

(57) ABSTRACT

A curved liquid crystal display comprises, a first curved substrate; a second curved substrate facing the first curved substrate; a liquid crystal layer disposed between the first curved substrate and the second curved substrate; a first curved liquid crystal alignment layer disposed between the liquid crystal layer and the first curved substrate and containing a light stabilizer; and a second curved liquid crystal alignment layer disposed between the liquid crystal layer and the second curved substrate.

18 Claims, 11 Drawing Sheets

(51) Int. Cl.
*C07D 211/46* (2006.01)
*C07D 211/22* (2006.01)
*C09K 19/54* (2006.01)
*C09K 19/34* (2006.01)
*C09K 19/56* (2006.01)
*C08G 73/10* (2006.01)

(52) U.S. Cl.
CPC ............ *C09K 19/56* (2013.01); *G02F 1/1341* (2013.01); *G02F 1/133788* (2013.01); *C09K 2019/548* (2013.01); *G02F 2001/133726* (2013.01); *G02F 2001/133742* (2013.01)

(58) Field of Classification Search
CPC .............. C09K 19/56; C09K 2019/548; Y10T 428/1005; Y10T 428/10
USPC ....... 349/123, 129, 144, 158, 191, 130, 178, 349/141, 43, 106; 428/1.2
See application file for complete search history.

(56) References Cited

U.S. PATENT DOCUMENTS

2014/0176856 A1\* 6/2014 Lee .................. G02F 1/133305 349/61
2017/0059941 A1\* 3/2017 Lee .................. G02F 1/133711

FOREIGN PATENT DOCUMENTS

| KR | 1020120098421 | 9/2012 |
| KR | 1020150002121 | 1/2015 |
| KR | 1020150012093 | 2/2015 |

\* cited by examiner

CURVED LIQUID CRYSTAL DISPLAY AND METHOD OF MANUFACTURING THE SAME

This application claims priority to Korean Patent Application No. 10-2015-0115881, filed on Aug. 18, 2015, and all the benefits accruing therefrom under 35 U.S.C. § an, the content of which in its entirety is herein incorporated by reference.

BACKGROUND

1. Field of the Invention

The present invention relates to a curved liquid crystal display and a method of manufacturing the same.

2. Description of the Related Art

Liquid crystal displays is a type of flat panel displays that is widely used. A liquid crystal display may include two substrates provided with electric field generating electrodes such as a pixel electrode, a common electrode, and the like, and a liquid crystal layer disposed between the substrates.

When a voltage is applied to an electric field generating electrode an electric field is generated in the liquid crystal layer whereby, the direction of alignment of the liquid crystals in the liquid crystal layer is determined and the polarization of incident light is controlled, thereby displaying an image.

When the liquid crystal display is used as a display device of a television receiver, a size of a screen thereof is enlarged. In accordance with the enlargement of the liquid crystal display, a difference in the angle of vision may be increased depending on whether a viewer watches a central portion of a screen or watches left and right sides of the screen.

In order to compensate for the difference in the angle of vision, a curved liquid crystal display may be formed by bending a liquid crystal display in a concave or a convex direction. The curved liquid crystal display may be a portrait type liquid crystal display having a length in a longitudinal direction greater than a length in a horizontal direction and curved in the longitudinal direction, based on a viewer. Alternatively, the curved liquid crystal display may be a landscape type liquid crystal display having a length in a longitudinal direction shorter than a length in a horizontal direction and curved in the horizontal direction.

SUMMARY

An aspect of embodiments of the present invention provides a curved liquid crystal display having improved light transmissivity, and a method of manufacturing the same.

In addition, another aspect of embodiments of the present invention provides a curved liquid crystal display capable of preventing the occurrence of unnecessary patterns or spots due to the application of a curved panel, and a method of manufacturing the same.

According to an exemplary embodiment, a curved liquid crystal display is provided. The curved liquid crystal display includes, a first curved substrate; a second curved substrate facing the first curved substrate; a liquid crystal layer disposed between the first curved substrate and the second curved substrate; a first curved liquid crystal alignment layer disposed between the liquid crystal layer and the first curved substrate and containing a light stabilizer; and a second curved liquid crystal alignment layer disposed between the liquid crystal layer and the second curved substrate.

In an exemplary embodiment, the second curved liquid crystal alignment layer may not contain the light stabilizer.

In an exemplary embodiment, the second curved includes a reactive mesogen and an amount of the reactive mesogen may be higher in the second curved liquid crystal alignment layer than an amount in the first curved liquid crystal alignment layer.

In an exemplary embodiment, the second curved liquid crystal alignment layer may have a multilayer structure including 2-$1^{st}$ curved liquid crystal alignment layer and a 2-$2^{nd}$ curved liquid crystal alignment layer including a reactive mesogen and an amount of the reactive mesogen is higher in the 2-$2^{nd}$ curved liquid crystal alignment layer than an amount in the 2-$1^{st}$ curved liquid crystal alignment layer.

In an exemplary embodiment, the light stabilizer may be represented by the following chemical formula 1:

Chemical Formula 1

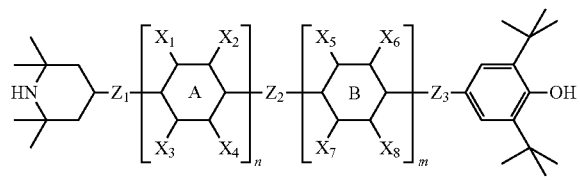

where n is 0 or 1, m is 0 or 1, Z1 to Z3 are each independently a single bond, a divalent alkenyl group, a divalent alkyl group, a divalent alkoxy group, —C(O)O—, or —$CF_2$O—; X1 to X8 are each independently an alkyl group, H, F, or $CF_3$; and A and B are each independently of the following formulas:

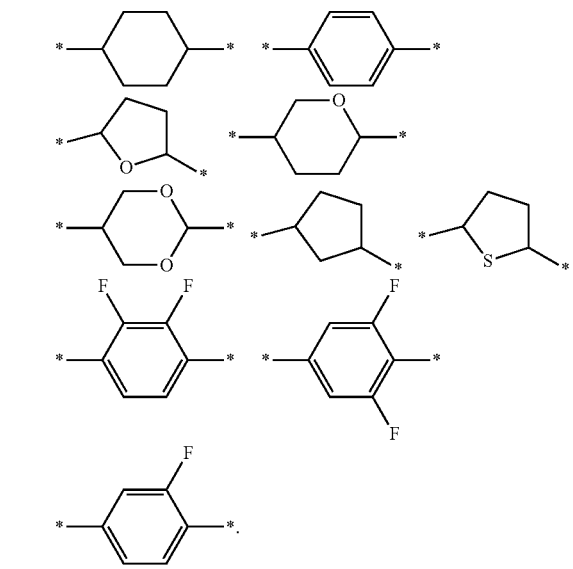

In an exemplary embodiment, in the chemical formula 1, Z1 to Z3 may each independently be a single bond, a divalent alkenyl group having 2 to 5 carbon atoms, a divalent alkyl group having 1 to 5 carbon atoms, a divalent alkoxy group, —C(O)O—, or —$CF_2$O—; and X1 to X8 are each independently $CH_3$, H, F, or $CF_3$.

In an exemplary embodiment, the light stabilizer may be represented by the following chemical formula 2:

The method of manufacturing a curved liquid crystal display, the light stabilizer may be represented by the following Chemical Formula 1:

Chemical Formula 1

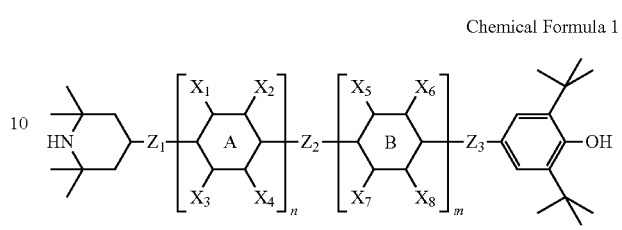

wherein n is 0 or 1; m is 0 or 1; Z1 to Z3 are each independently a single bond, a divalent alkenyl group, a divalent alkyl group, a divalent alkoxy group, —C(O)O—, or —CF$_2$O—; X1 to X8 are each independently an alkyl group, H, F, or CF$_3$, and A and B are each independently of the formulas:

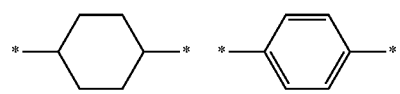

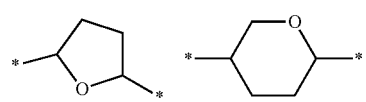

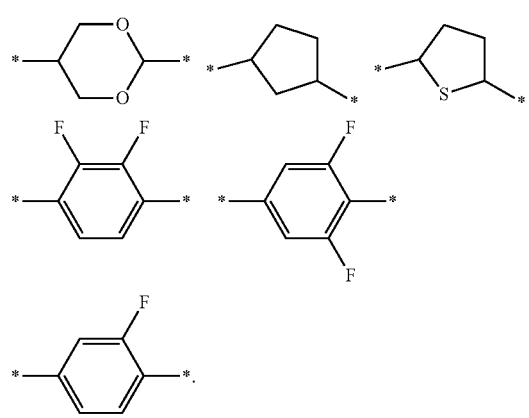

In an exemplary embodiment of manufacturing a curved liquid crystal display, in the Chemical Formula 1, Z1 to Z3 may each independently be a single bond, a divalent alkenyl group having 2 to 5 carbon atoms, a divalent alkyl group having 1 to 5 carbon atoms, a divalent alkoxy group, —C(O)O—, or —CF$_2$O—; and X1 to X8 are each independently CH$_3$, H, F, or CF$_3$.

In an exemplary embodiment of manufacturing a curved liquid crystal display, the light stabilizer may be represented by the following chemical formula 2.

Chemical Formula 2

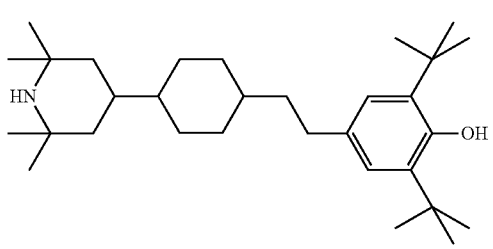

In an exemplary embodiment, the light stabilizer may be represented by the following chemical formula 3:

Chemical Formula 3

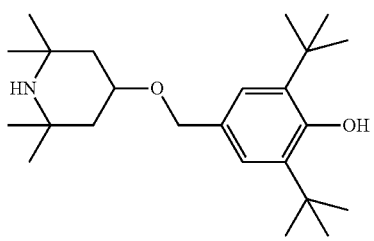

In an exemplary embodiment, the light stabilizer may be present as a side chain of a polyimide in the first curved liquid crystal alignment layer.

The curved liquid crystal display, the light stabilizer may be present in an amount of greater than 0 parts per million (ppm) and equal to or less than about 10,000 ppm with respect to an overall weight of the first curved liquid crystal alignment layer.

In an exemplary embodiment, the liquid crystal layer may include first liquid crystal molecules having negative dielectric constant anisotropy aligned with a surface of the first curved liquid crystal alignment layer, and second liquid crystal molecules aligned with a surface of the second curved liquid crystal alignment layer, and where the first liquid crystal molecules may be vertically aligned as compared to the second liquid crystal molecules when an electrical field is not applied to the liquid crystal layer.

In an exemplary embodiment, the curved liquid crystal display may further include, a patternless electrode disposed between the first curved substrate and the first curved liquid crystal alignment layer and having no slit pattern; and a pattern electrode disposed between the second curved liquid crystal alignment layer and the second curved substrate and having a slit pattern.

According to another exemplary embodiment, a method of manufacturing a curved liquid crystal display includes, preparing a first curved substrate and a second curved substrate facing each other; forming a first curved liquid crystal alignment layer on a surface of the first curved substrate facing the second curved substrate; forming a second curved liquid crystal alignment layer on a surface of the second curved substrate facing the first curved substrate; injecting a liquid crystal composition into a space between the first curved substrate and the second curved substrate; and irradiating ultraviolet light in a direction toward at least one of the first curved substrate and the second curved substrate when an electric field is applied, wherein the first curved liquid crystal alignment layer contains a light stabilizer.

Chemical Formula 2

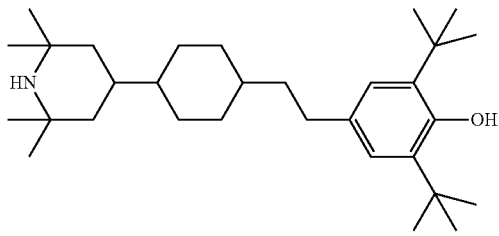

In an exemplary embodiment of manufacturing a curved liquid crystal display, the light stabilizer may be represented by the following chemical formula 3.

Chemical Formula 3

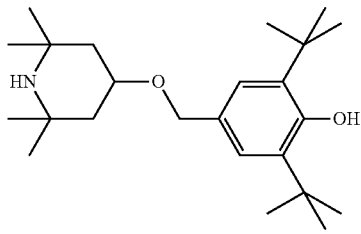

In an exemplary embodiment of manufacturing a curved liquid crystal display, the light stabilizer may be present in an amount of greater than 0 ppm and equal to or less than about 10,000 ppm with respect to an overall weight of the first curved liquid crystal alignment layer.

In an exemplary embodiment of manufacturing a curved liquid crystal display, at least one of the first curved liquid crystal alignment layer, the second curved liquid crystal alignment layer, and the liquid crystal composition may contain a reactive mesogen.

In an exemplary embodiment of manufacturing a curved liquid crystal display, due to the irradiating of ultraviolet light, the second curved liquid crystal alignment layer may have a multilayer structure including a 2-$1^{st}$ curved liquid crystal alignment layer and a 2-$2^{nd}$ curved liquid crystal alignment layer, and an amount of reactive mesogen in the 2-$2^{nd}$ curved liquid crystal alignment layer is higher than an amount in the 2-$1^{st}$ curved liquid crystal alignment layer.

BRIEF DESCRIPTION OF DRAWINGS

The above and other aspects and features of the various embodiments will become more apparent by describing in detail exemplary embodiments thereof with reference to the attached drawings, in which.

DETAILED DESCRIPTION

Figure 1:
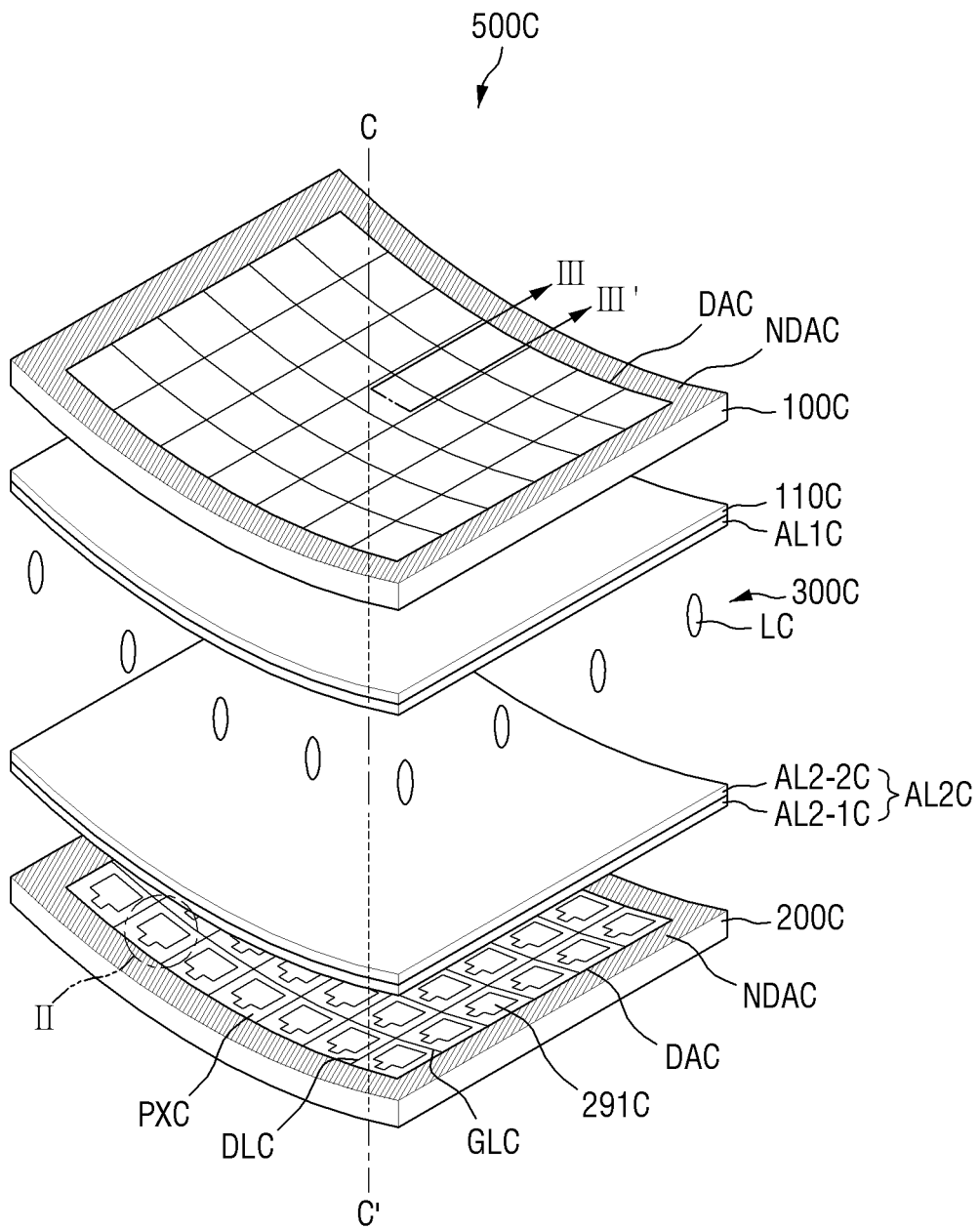
FIG. 1 is a schematic exploded perspective view of an exemplary embodiment of curved liquid crystal display.

Features of the inventive concept and methods of accomplishing the same may be understood more readily by reference to the following detailed description of preferred embodiments and the accompanying drawings.

The inventive concept may, however, be embodied in many different forms and should not be construed as being limited to the embodiments set forth herein. Rather, these embodiments are provided so that this disclosure will be thorough and complete and will fully convey the concept of the inventive concept to those skilled in the art, and the inventive concept will only be defined by the appended claims.

In the drawings, the thickness of layers and regions are exaggerated for clarity. It will be understood that when an element or layer is referred to as being "on," "connected to" or "coupled to" another element or layer, the element or layer can be directly on, connected or coupled to another element or layer or intervening elements or layers. In contrast, when an element is referred to as being "directly on," "directly connected to" or "directly coupled to" another element or layer, there are no intervening elements or layers present. As used herein, connected may refer to elements being physically, electrically and/or fluidly connected to each other.

Like numbers refer to like elements throughout. In order to distinguish between flat liquid crystal display and curved liquid crystal display, reference number of a curved liquid crystal display and elements of the same are represented by "C." As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer, or section discussed below could be termed a second element, component, region, layer, or section without departing from the teachings of the invention.

Spatially relative terms, such as "bottom," "below," "lower," "under," "above," "upper," "top," and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "below" or "beneath" relative to other elements or features would then be oriented "above" relative to the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a," "an" and "the" are intended to include the plural forms as well, unless the context clearly indicates otherwise. "Or"

means "and/or, unless the context clearly indicates otherwise. It will be further understood that the terms "comprises," "comprising," "includes" and/or "including," when used in this specification, specify the presence of stated features, integers, operations, elements, and/or components, but do not preclude the presence or addition of one or more other features, integers, steps, operations, elements, components, and/or groups thereof.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value."

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Hereinafter, exemplary embodiments will be described in detail with reference to the attached drawings.

Figure 2:
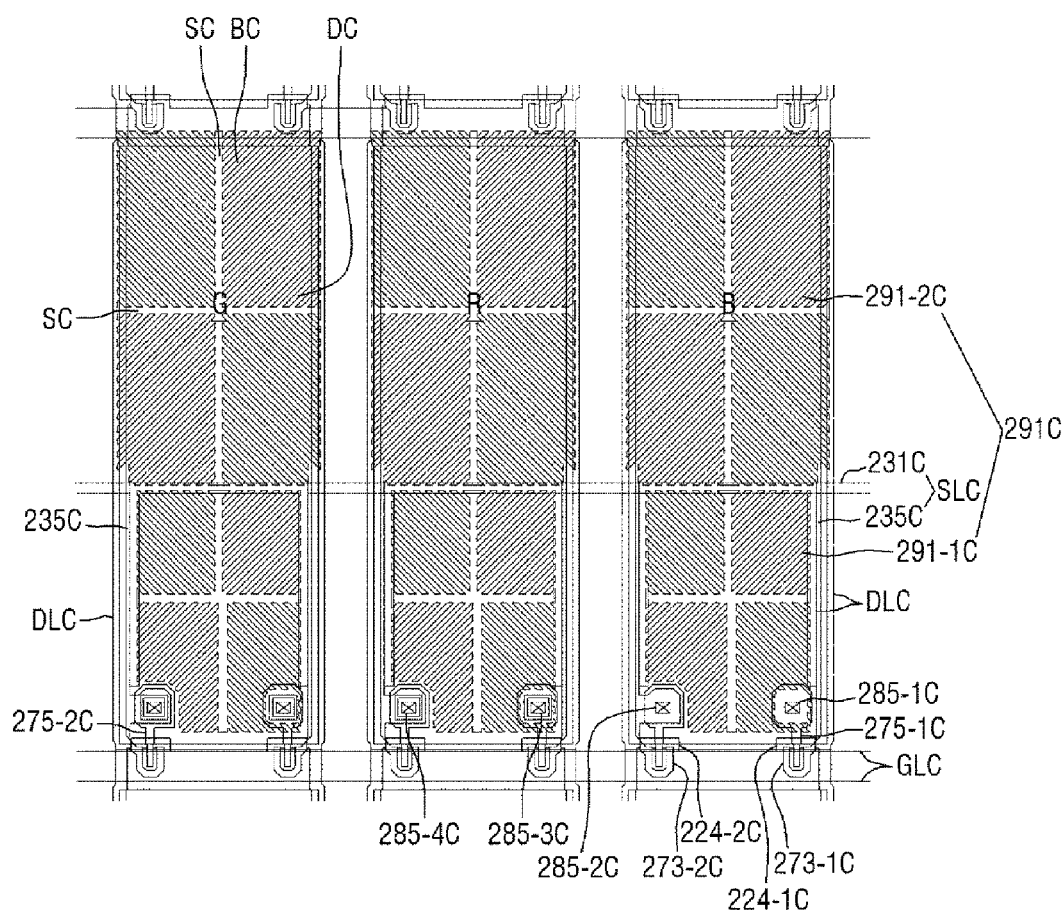
FIG. 2 is a schematic enlarged view of region II of FIG. 1.

FIG. 1 is a schematic exploded perspective view of an exemplary embodiment of a curved liquid crystal display 500C. FIG. 2 is a schematic enlarged view of region II of FIG. 1.

Referring to FIG. 1 and FIG. 2, the exemplary curved liquid crystal display 500C may include a first curved substrate 100C, a second curved substrate 200C spaced apart from and facing the first curved substrate 100C, and a liquid crystal layer 300C disposed between the first curved substrate 100C and the second curved substrate 200C.

Each of the first curved substrate 100C and the second curved substrate 200C may include a display region DAC and a non-display region NDAC. The display region DAC may be an image-visible region, and the non-display region NDAC may be an image-invisible region. An edge of the display region DAC may be surrounded by the non-display region NDAC.

A common electrode 110C may be disposed between the first curved substrate 100C and the second curved substrate 200C and may be a patternless electrode having no slit pattern. Pixel electrodes 291C may be disposed between the second curved substrate 200C and the common electrode 110C and may be pattern electrodes having a slit pattern.

The liquid crystal layer 300C may be disposed between the common electrode 110C and the pixel electrodes 291C. The liquid crystal layer 300C may include liquid crystal molecules LC having negative dielectric constant anisotropy. A first curved liquid crystal alignment layer AL1C may be disposed between the common electrode 110C and the liquid crystal layer 300C, and a second curved liquid crystal alignment layer AL2C may be disposed between the pixel electrodes 291C and the liquid crystal layer 300C.

The second curved substrate 200C may be a thin film transistor substrate. In the display region DAC of the second curved substrate 200C, a plurality of gate lines GLC extended in a first direction and a plurality of data lines DLC extended in a second direction perpendicular to the first direction may be formed. The pixel electrodes 291C may be disposed in respective pixels PXC defined by the gate lines GLC and the data lines DLC.

Each of the pixel electrodes 291C may include sub-pixel electrodes 291-1C and 291-2C spaced apart from each other. In an exemplary embodiment, each of the sub-pixel electrodes 291-1C and 291-2C may have a generally quadrangular shape and may be a pattern electrode having a slit pattern. In detail, the slit pattern may be configured to include a stem portion SC and a cut portion DC disposed between branch portions BC extended from the stem portion SC. The stem portion SC may be formed in a cross (+) shape, and the branch portions BC may be radially extended in a direction of approximately 45° from the cross (+) shaped stem portion SC.

The gate lines GLC may include gate electrodes 224-1C and 224-2C protruding from the gate lines GLC toward the pixel electrodes 291C in the second direction. The plurality of data lines DLC may include source electrodes 273-1C and 273-2C and drain electrodes 275-1C and 275-2C. The source electrodes 273-1C and 273-2C may protrude from the data lines DLC and may be respectively formed in a U-shape. The drain electrodes 275-1C and 275-2C may be disposed to be spaced apart from the source electrodes 273-1C and 273-2C.

The pixel electrodes 291C may receive a data voltage through a thin film transistor, a switching device. The gate electrodes 224-1C and 224-2C, which are control terminals of the thin film transistor, may be electrically connected to the gate lines GLC. The source electrodes 273-1C and 273-2C, which are input terminals of the thin film transistor, may be electrically connected to the data lines DLC via contact holes 285-1C, 285-2C, 285-3C, and 285-4C. The drain electrodes 275-1C and 275-2C, which are output terminals of the thin film transistor, may be electrically connected to the pixel electrodes 291C.

The pixel electrodes 291C, together with the common electrode 110C may generate an electric field to control the direction of alignment of the liquid crystal molecules LC in the liquid crystal layer 300C disposed between the pixel electrodes 291C and the common electrode 110C. The pixel electrodes 291C may distort an electric field to control the direction of alignment of first liquid crystal molecules LC1 and second liquid crystal molecules LC2.

The thin film transistor substrate may have a structure in which a base substrate (not shown) formed of glass or a polymer, the gate electrodes 224-1C and 224-2C, a gate insulating layer (not shown), a semiconductor layer (not shown), an ohmic-contact layer (not shown), the source electrodes 273-1C and 273-2C, the drain electrodes 275-1C and 275-2C, a passivation layer (not shown), an organic layer (not shown), and the like, are stacked.

A channel of the thin film transistor may be formed of the semiconductor layer (not shown). The semiconductor layer (not shown) may be disposed to overlap with the gate electrodes 224-1C and 224-2C. The respective source electrodes 273-1C and 273-2C and the respective drain electrodes 275-1C and 275-2C may be spaced apart from each other based on the semiconductor layer (not shown).

A storage electrode line SLC may include a stem line 231C disposed to be substantially parallel to the plurality of gate lines GLC and a plurality of branch lines 235C extended from the stem line 231C. The storage electrode line SLC may be omitted, and the shape and disposition thereof may be variously modified.

The non-display region NDAC, which is the periphery of the display region DAC, may be a light-shielding region surrounding the display region DAC. In the non-display region NDAC of the second curved substrate 200C, a driver (not shown) providing a gate driving signal, a data driving signal, and the like to the respective pixels PXC may be disposed. The gate lines GLC and the data lines DLC may be extended from the display region DAC to the non-display region NDAC and may be electrically connected to the driver (not shown).

The first curved substrate 100C may be a substrate facing the second curved substrate 200C. The common electrode 110C may be disposed on the second curved substrate 200C.

A color filter layer (not shown) may be formed in a region corresponding to the respective pixels PXC in the display region DAC and may include a red color filter R, a green color filter G, and a blue color filter B. The color filter layer (not shown) may be included in one of the first curved substrate 100C and the second curved substrate 200C. For example, when the first curved substrate 100C includes the color filter layer, the first curved substrate 100C may have a structure in which a base substrate (not shown) formed of glass or a polymer, the color filter layer (not shown), and an overcoating layer (not shown) are stacked. The overcoating layer (not shown) may be a planarization layer covering the color filter layer (not shown). In this case, the common electrode 110C may be disposed on the overcoating layer (not shown).

For example, in the case that the second curved substrate 200C includes the color filter layer (not shown), the second curved substrate 200C may have a color filter on array (COA) structure in which a color filter is formed on a transparent insulating substrate. For example, the color filter layer (not shown) may be disposed between a passivation layer (not shown) covering the source electrodes 273-1C and 273-2C and the drain electrodes 275-1C and 275-2C, and an organic layer (not shown).

A light-shielding pattern layer (not shown) may be formed in boundary portions of the respective color filters R, G, and B. The light-shielding pattern layer (not shown) may be included in one of the first curved substrate 100C and the second curved substrate 200C. For example, the light-shielding pattern layer (not shown) may be a black matrix.

In a process of bending a flat liquid crystal display at the time of manufacturing the curved liquid crystal display 500C, a misalignment between the first and second curved substrates 100C and 200C may be caused due to stress applied to each of the first and second curved substrates 100C and 200C. For example, in the process of bending a flat liquid crystal display, the first curved substrate 100C may be shifted leftward or rightward with respect to the second curved substrate 200C. When this happens, a disposition state of the first and second curved substrates 100C and 200C may be altered from a predesigned disposition state of the first and second curved substrates 100C and 200C. Such a misalignment between the first and second curved substrates 100C and 200C may degrade the display quality of the curved liquid crystal display 500C.

For example, when the first curved liquid crystal alignment layer AL1C and the second curved liquid crystal alignment layer AL2C each includes a plurality of domains in which the directors of liquid crystal molecules are aligned in directions different from each other, a misalignment occurs between a boundary portion of the domains of the first curved liquid crystal alignment layer AL1C and a boundary portion of the domains of the second curved liquid crystal alignment layer AL2C. This misalignment may cause interference or collision in the direction of alignment between the first liquid crystal molecules, which are inclinedly (i.e. tilt) aligned on the surface of the first curved liquid crystal alignment layer AL1C, and the second liquid crystal molecules which are inclinedly aligned on a surface of the second curved liquid crystal alignment layer AL2C in a direction different from that of the first liquid crystal molecules. As a result, liquid crystal molecules positioned between the first and second liquid crystal molecules may be substantially, vertically aligned to form a texture. The texture may be viewed as a spot or a dark space in the display region DAC of the curved liquid crystal display 500C, and as a result, light transmissivity of the curved liquid crystal display 500C may be degraded.

Figure 3:
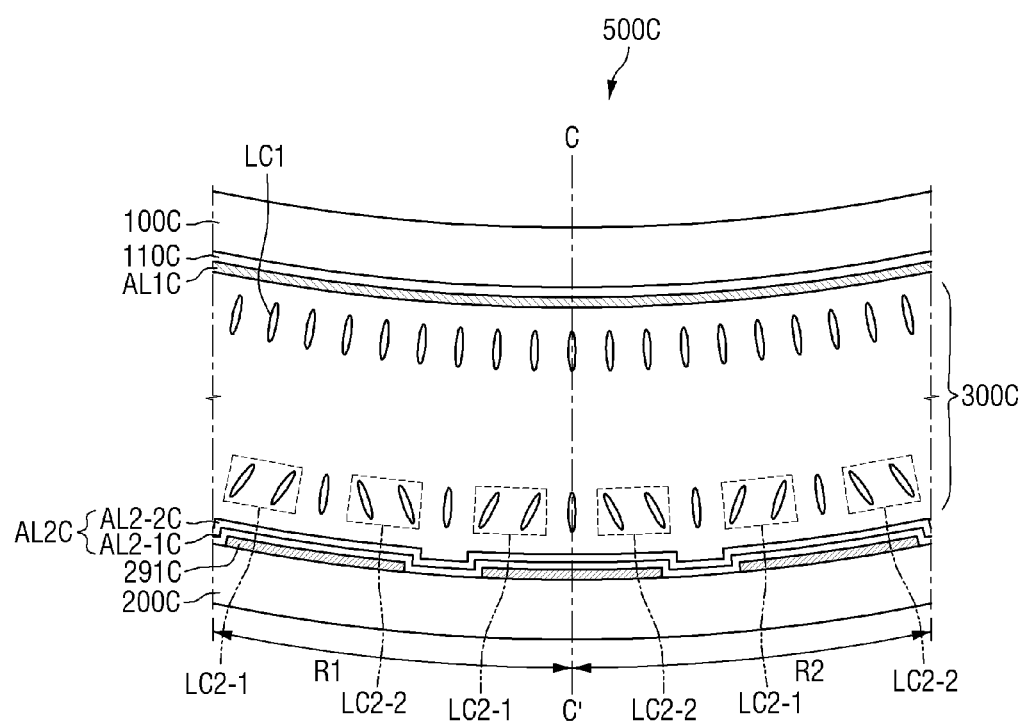
FIG. 3 is a schematic cross-sectional view, taken along line of FIG. 1.

FIG. 3 is a schematic cross-sectional view, taken along line of FIG. 1. Hereinafter, the exemplary curved liquid crystal display 500C will be described in more detail, with reference to FIG. 3. FIG. 3 schematically illustrates the alignment of the liquid crystal molecules LC1, LC2-1, and LC2-2 in an initial state in which an electric field is not applied to the curved liquid crystal display 500C.

Referring to FIG. 3, the first liquid crystal molecules LC1 may be aligned at the surface of the first curved liquid crystal alignment layer AL1C. The second liquid crystal molecules LC2-1 and LC2-2 may be aligned at the surface of the second curved liquid crystal alignment layer AL2C. The first liquid crystal molecules LC1 may be relatively vertically aligned as compared to the second liquid crystal molecules LC2-1 and LC2-2. That is, the second liquid crystal molecules LC2-1 and LC2-2 may be relatively aligned at an incline (i.e. tilted) as compared to the first liquid crystal molecules LC1.

In other words, the second liquid crystal molecules LC2-1 and LC2-2 may be aligned at a predetermined pretilt angle at the surface of the second curved liquid crystal alignment layer AL2C. Unlike the second liquid crystal molecules LC2-1 and LC2-2, the first liquid crystal molecules LC1 may be arranged in a state in which a pretilt is not implemented or is hardly implemented. That is, liquid crystal molecules LC1 may only be aligned substantially vertically. Accordingly, even when the misalignment occurs in a process of bending the first and second curved substrates 100C and 200C, interference or collision in directions of alignment may be prevented and formation of the above-mentioned texture may be prevented. Thus, defects in which the texture may be viewed as a spot or a dark space in the display region DAC of the curved liquid crystal display 500C, and where light transmissivity of the curved liquid crystal display 500C may be degraded, may be prevented.

By way of example, in the initial state in which an electric field is not applied to the curved liquid crystal display 500C, the second curved liquid crystal alignment layer AL2C may form at least two or more domains in which alignment directions of the second liquid crystal molecules LC2-1 and LC2-2 are different from each other. These two domains are referred to as a first region R1 and a second region R2. Alternatively, the first curved liquid crystal alignment layer AL1C may form a single domain in which alignment directions of the first liquid crystal molecules LC1 are substantially identical to each other in each of the first region R1 and the second region R2.

The first region R1 and the second region R2 refer to a left region and a right region, respectively, based on a virtual straight line C-C' passing through a peak of the first curved substrate 100C and a peak of the second curved substrate 200C. The peak, an optional point on a curved line, may refer to a point at which the slope of the tangent line is substantially zero.

Referring to FIG. 3, in the first region R1, the 2-$1^{st}$ liquid crystal molecules LC2-1 of the second curved liquid crystal alignment layer AL2C may be aligned in a first inclination direction, and the 2-$2^{nd}$ liquid crystal molecules LC2-2 of the second curved liquid crystal alignment layer AL2C may be aligned in a second inclination direction. In the first region R1, the second curved liquid crystal alignment layer AL2C may form at least two or more domains in which the alignment direction of the 2-$1^{st}$ liquid crystal molecules LC2-1 and the alignment direction of the 2-$2^{nd}$ liquid crystal molecules LC2-2 are different from each other. The first inclination direction may be a direction of approximately −α° with respect to the virtual straight line C-C', and the second inclination direction may be a direction of approximately +α° with respect to the virtual straight line C-C'. The α is a positive real number.

In the second region R2, the 2-$1^{st}$ liquid crystal molecules LC2-1 of the second curved liquid crystal alignment layer AL2C may be aligned in the first inclination direction, and the 2-$2^{nd}$ liquid crystal molecules LC2-2 of the second curved liquid crystal alignment layer AL2C may be aligned in the second inclination direction. In the second region R2, the second curved liquid crystal alignment layer AL2C may form at least two or more domains in which the alignment direction of the 2-$1^{st}$ liquid crystal molecules LC2-1 and the alignment direction of the 2-$2^{nd}$ liquid crystal molecules LC2-2 are different from each other.

Meanwhile, in the first region R1, the first curved liquid crystal alignment layer AL1C may form a single domain in which the first liquid crystal molecules LC1 are aligned in a third inclination direction. In the second region R2, the first curved liquid crystal alignment layer AL1C may form a single domain in which the first liquid crystal molecules LC1 are aligned in a fourth inclination direction. For example, the third inclination direction may be a direction of approximately 43° with respect to the virtual straight line C-C', and the fourth inclination direction may be a direction of approximately +β° with respect to the virtual straight line C-C'. The β is a positive real number.

In this manner, in each of the first region R1 and the second region R2, only the second curved liquid crystal alignment layer AL2C of the first and second curved liquid crystal alignment layers AL1C and AL2C may be provided with a plurality of domains in which the alignment directions of the liquid crystal molecules are different from each other. Accordingly, the occurrence of a stain or a dark portion caused by the collision of the alignment directions of the first liquid crystal molecules LC1 and the second liquid crystal molecules LC2-1 and LC2-2 may be improved.

The first curved liquid crystal alignment layer AL1C may contain a light stabilizer. On the other hand, the second curved liquid crystal alignment layer AL2C may not contain a light stabilizer. The light stabilizer may inhibit a radical polymerization of a reactive mesogen that may be present within an alignment layer or a liquid crystal, thereby preventing a pretilt from being provided to the liquid crystal. In the case of the exemplary curved liquid crystal display, the light stabilizer may be contained in the first curved liquid crystal alignment layer AL1C to inhibit polymerization of reactive mesogen while the light stabilizer may not be included in the second curved liquid crystal alignment layer AL2C to allow for the polymerization of the reactive mesogen. Accordingly, the amount of reactive mesogen may be higher in the second curved liquid crystal alignment layer AL2C than in the first curved liquid crystal alignment layer AL1C.

Meanwhile, when the amount of reactive mesogen in the second curved liquid crystal alignment layer AL2C is higher than in the first curved liquid crystal alignment layer AL1C as described above, a pretilt angle may be greater in the second curved liquid crystal alignment layer AL2C than in the first curved liquid crystal alignment layer AL1C. Alternatively, a degree of roughness on the surface of the second curved liquid crystal alignment layer AL2C may be higher than that of the first curved liquid crystal alignment layer AL1C.

In other words, the second curved liquid crystal alignment layer AL2C may contain no light stabilizer, such that the polymerization of reactive mesogen may be more actively generated and accordingly, the pretilt angle may be increased. Further, due to the polymerized reactive mesogen, a degree of surface roughness on the second curved liquid crystal alignment layer AL2C may be increased as compared to the first curved liquid crystal alignment layer AL1C. This can be understood to mean that the amount of protrusions due to polymerization of the reactive mesogen compound in the second curved liquid crystal alignment layer AL2C is increased.

In order to confirm reactivity of the reactive mesogen as described above, the degree of surface roughness (average-rough, Rp-v, and Rms rough) and pretilt angles were measured in a case in which a light stabilizer is not present and in cases in which a light stabilizer (the light stabilizer of the Chemical Formula 2) is present. The light stabilizer is included in an amount of 0 ppm, 300 ppm, and 1000 ppm. The measured results are indicated in the following Table 1.

TABLE 1

|  | The amount of light stabilizer (ppm) | | |
| --- | --- | --- | --- |
|  | 0 ppm | 300 ppm | 1000 ppm |
| Average-roughness (nanometers, nm) | 13.9 nm | 7.8 nm | 5.3 nm |
| Rp-v (maximum deviation) | 122.7 nm | 119.0 nm | 110.9 nm |
| Rms rough (mean square roughness) | 17.2 | 10.7 | 8.6 |
| Pretilt angle (°) | 87° | 87.9° | 88.8° |

As shown in Table 1, it could be confirmed that the pretilt angle was decreased and the surface roughness was lowered in accordance with an increase in the amount of the light stabilizer, when compared to the case of having no light stabilizer (0 ppm). Without being limited by theory, it is believed that the increase in the amount of the light stabilizer results in a decrease in the amount of reactive mesogen polymerization leading to the decrease in the pretilt angle. Further, due to the lower amount of reactive mesogen polymerization, the amount of protrusions caused by the reaction of the reactive mesogen compound was relatively low, thereby resulting in a decrease in surface roughness.

The light stabilizer may be contained in an amount of greater than 0 ppm and equal to or less than about 10,000 ppm with respect to the overall weight of the first curved liquid crystal alignment layer AL1C. For example, the light stabilizer may be present in an amount of greater than 0 ppm and equal to or less than about 1200 ppm, or more specifically, in an amount of about 100 ppm to about 1000 ppm. As the liquid crystals are appropriately, vertically aligned within the range in the amount of the light stabilizer, a difference in the pretilt angles of the first curved liquid crystal alignment layer AL1C and the second curved liquid crystal alignment layer AL2C may be provided. However, the amount of light stabilizer is not limited to the ranges described above.

The light stabilizer may be characterized as a compound represented by the following Chemical Formula 1.

Chemical Formula 1

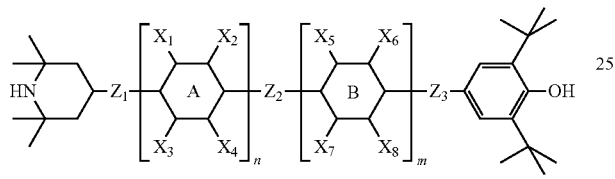

In the Chemical Formula 1, n is 0 or 1; m is 0 or 1; Z1 to Z3 are each independently a single bond, a divalent alkenyl group, a divalent alkyl group, a divalent alkoxy group, —C(O)O—, or —CF$_2$O—; X1 to X8 are each independently an alkyl group, H, F, or CF$_3$; and A and B are each independently of the following formulas.

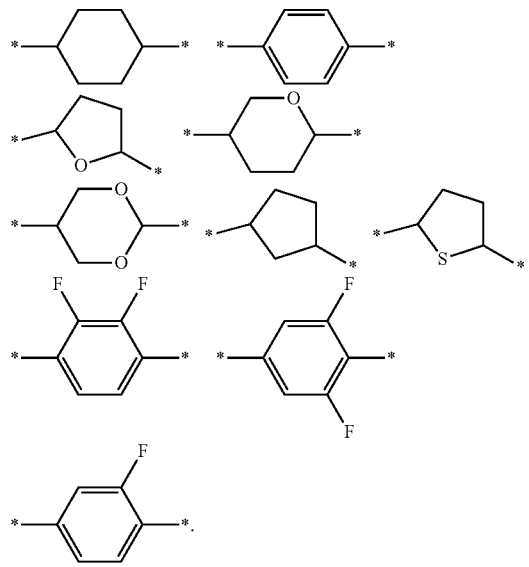

Further in Chemical Formula 1, the divalent alkenyl group may have 2 to 18 carbon atoms, or 2 to 12 carbon atoms, or 2 to 8 carbon atoms. The divalent alkyl group may have 1 to 18 carbon atoms, or 1 to 12 carbon atoms, or 1 to 8 carbon atoms The divalent alkoxy group may have 1 to 18 carbon atoms, or 1 to 12 carbon atoms, or 1 to 8 carbon atoms. In some embodiments, the divalent alkoxy group is linked via the oxygen atom and a carbon atom of the alkyl group.

Specifically, in Chemical Formula 1, Z1 to Z3 are each independently a single bond, a divalent alkenyl group having 2 to 5 carbon atoms, a divalent alkyl group having 1 to 5 carbon atoms, a divalent alkoxy group having 1 to 5 carbon atoms, —C(O)O—, or —CF$_2$O—, and X1 to X8 are each independently CH$_3$, H, F, or CF$_3$.

More specifically, the light stabilizer may be a compound represented by the following chemical formula 2.

Chemical Formula 2

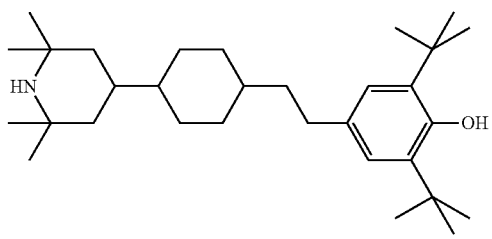

In addition, the light stabilizer may be a compound represented by the following chemical formula 3.

Chemical Formula 3

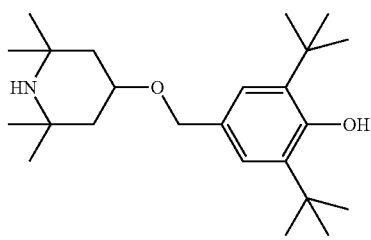

The light stabilizer may be in a form in which it is present as a side chain of a polyimide, i.e., in a derivatized form. In some embodiments the light stabilizer may be covalently linked to a the main chain of a polyimide in the first curved liquid crystal alignment layer AL1C, and in other embodiments the light stabilizer may be covalently linked to a side chain of a polyimide in the first curved liquid crystal alignment layer AL1C. Thus, when the first curved liquid crystal alignment layer AL1C contains reactive mesogen therein, or when liquid crystals are injected into the first curved liquid crystal alignment layer AL1C while the liquid crystals contain reactive mesogen therein, it may be possible to prevent polymerization of the mesogen between the first curved liquid crystal alignment layer AL1C and the liquid crystals.

The first curved liquid crystal alignment layer AL1C may be, for example, a vertically aligned liquid crystal alignment layer containing a polyimide in which an imide group (—CONHCO—) is included as a repeating unit in a main chain thereof. At least one vertical alignment group, in particular an alkyl group, a hydrocarbon derivative having an end substituted with the alkyl group, a hydrocarbon derivative having an end substituted with a cycloalkyl group, and a hydrocarbon derivative having an end substituted with an aromatic hydrocarbon, is present as a side chain thereof. The foregoing vertical alignment groups can have from 6 to 60 carbon atoms.

The first curved liquid crystal alignment layer AL1C may include, for example, repeating units derived from a dianhydride such as those represented by following Chemical Formula 4.

Chemical Formula 4

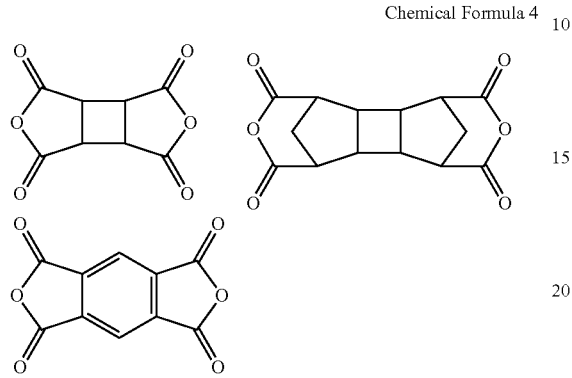

In addition, the first curved liquid crystal alignment layer AL1C may include, for example, repeating units derived from a diamine such as those represented by the following Chemical Formula 5, such that liquid crystals may be vertically aligned.

Chemical Formula 5

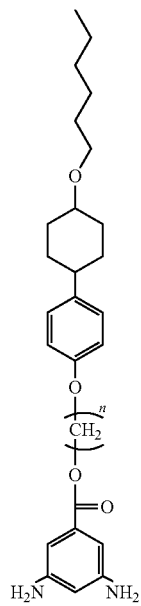

-continued

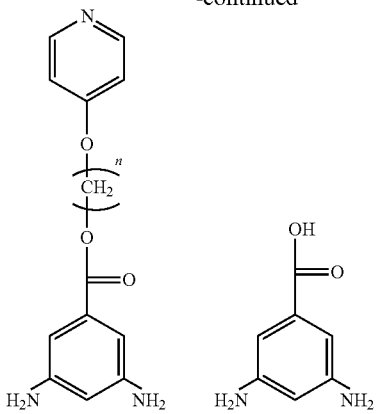

In Chemical Formula 5, each n may independently be a natural number of 1 to 20. The light stabilizer may be present as a side chain of the polyimide of the first curved liquid crystal alignment layer AL1C and particularly, may be present as a side chain of one of diamine repeating units like the chemical formula 5.

Meanwhile, the mesogen may be, for example, a compound having a structure of the following Chemical Formula 6, but is not limited thereto.

P-sp-A1-(A2)m-sp-P      Chemical Formula 6

In Chemical Formula 6, m is a natural number of 1 to 3, each P is independently a polymerizable group, sp is a spacer group, and A1 and A2 are each independently an unsubstituted phenyl group or a thiophene group, or a hydrogen bonded to the phenyl group or thiophene group is substituted with F, Cl, —OCH$_3$, or an alkyl group having 1 to 6 carbon atoms.

Specifically, the reactive mesogen may be, for example, a compound having the structure of Chemical Formulas 7 or 8, but is not limited thereto.

Chemical Formula 7

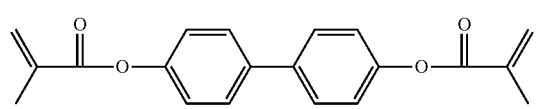

Chemical Formula 8

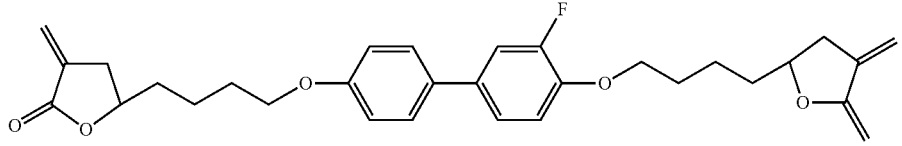

The second curved liquid crystal alignment layer AL2C is different from the first curved liquid crystal alignment layer AL1C in that it contains no light stabilizer and the light stabilizer is not present as the side chain of the polyimide.

Meanwhile, the second curved liquid crystal alignment layer AL2C may have a multilayer structure including a 2-$1^{st}$ curved liquid crystal alignment layer AL2-1C and a 2-$2^{nd}$ curved liquid crystal alignment layer AL2-2C having an amount of reactive mesogen higher than the amount of reactive mesogen in the 2-$1^{st}$ curved liquid crystal alignment layer AL2-1C. That is, the second curved liquid crystal alignment layer AL2C may not include an element inhibiting the radical polymerization of the reactive mesogen, and as such, the radical polymerization of reactive mesogen may be actively performed. Thus, in the second curved liquid crystal alignment layer AL2C, the 2-$1^{st}$ curved liquid crystal alignment layer AL2-1C including vertical alignment elements may be formed, and on an upper portion thereof, the 2-$2^{nd}$ curved liquid crystal alignment layer AL2-2C providing the pretilt of liquid crystals may be formed by the polymerization of reactive mesogen.

The second liquid crystal molecules LC2-1 and LC2-2 positioned on an upper portion of the 2-$2^{nd}$ curved liquid crystal alignment layer AL2-2C may be aligned at a predetermined pretilt angle at the surface of the second curved liquid crystal alignment layer AL2C, that is, on the 2-$2^{nd}$ curved liquid crystal alignment layer AL2-2C.

Meanwhile, the 2-$2^{nd}$ curved liquid crystal alignment layer AL2-2C may be partially formed on a surface of the 2-$1^{st}$ curved liquid crystal alignment layer AL2-1C.

For example, the 2-$1^{st}$ curved liquid crystal alignment layer AL2-1C may be a vertically aligned liquid crystal alignment layer containing an imide group (—CONHCO—) as a repeating unit in the main chain thereof, and a vertical alignment group as a side chain thereof. The 2-$2^{nd}$ curved liquid crystal alignment layer AL2-2C may be a polymer of the reactive mesogens.

The amount of the imide group may be higher in the 2-$1^{st}$ curved liquid crystal alignment layer AL2-1C than in the 2-$2^{nd}$ curved liquid crystal alignment layer AL2-2C, and the amount of reactive mesogen may be higher in the 2-$2^{nd}$ curved liquid crystal alignment layer AL2-2C than in the 2-$1^{st}$ curved liquid crystal alignment layer AL2-1C.

Meanwhile, an embodiment in which the light stabilizer is contained in the first curved liquid crystal alignment layer AL1C but is not contained in the 2-$1^{st}$ curved liquid crystal alignment layer AL2-1C, is described above. However, other embodiments in which the light stabilizer is contained in the 2-$1^{st}$ curved liquid crystal alignment layer AL2-1C but is not contained in the first curved liquid crystal alignment layer AL1C, may also be applicable.

FIG. 4 through FIG. 9 are cross-sectional views illustrating an exemplary embodiment of a method of manufacturing a curved liquid crystal display. Hereinafter, the method of manufacturing the curved liquid crystal display 500C will be described with reference to FIG. 4 through FIG. 9.

Figure 4:
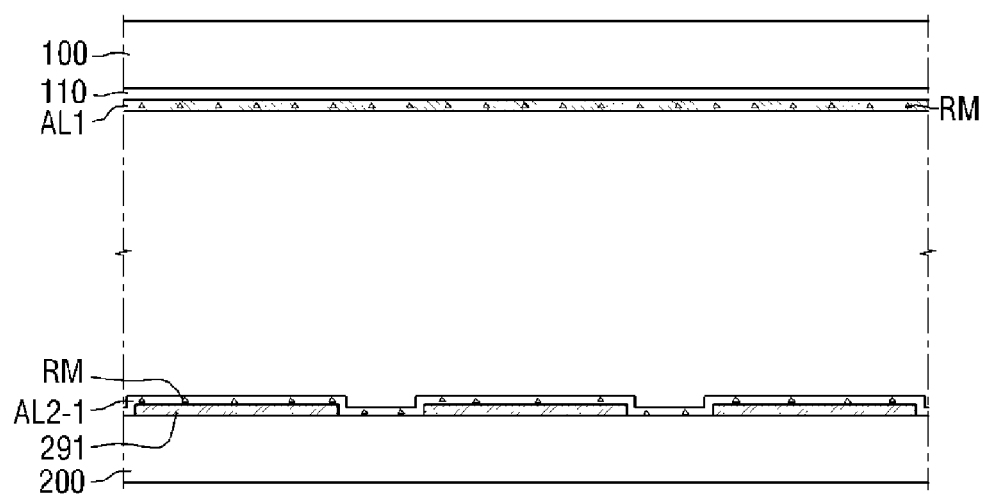
FIG. 4 through FIG. 9 are cross-sectional views illustrating an exemplary embodiment of a method of manufacturing a curved liquid crystal display.

Referring to FIG. 4, a first flat substrate 100 may be disposed to face a second flat substrate 200 while maintaining a predetermined cell gap therebetween. For example, the second flat substrate 200 may be a thin film transistor substrate, and the first flat substrate 100 may be a color filter substrate.

The common electrode 110C may be disposed on the first flat substrate 100, and a first flat liquid crystal alignment layer AL1 may be disposed on the common electrode 110. The common electrode 110 may be configured of one or more of an indium tin oxide, an indium zinc oxide, an indium oxide, a zinc oxide, a tin oxide, a gallium oxide, a titanium oxide, aluminum, silver, platinum, chromium, molybdenum, tantalum, niobium, zinc, magnesium, alloys thereof, and stack layers thereof. As described previously, the common electrode 110 may be a patternless electrode having no slit pattern.

The first flat liquid crystal alignment layer AL1 may be formed by, for example, applying a complex liquid crystal alignment agent containing a first vertically aligned polyimide having a vertical alignment group present as a side chain thereof, a reactive mesogen RM, and a light stabilizer, onto the common electrode 110 and then drying the same. In this case, the first vertically aligned polyimide may contain an imide group (—CONHCO—) as a repeating unit of a main chain thereof and may only include the vertical alignment group in the side chain thereof. The light stabilizer is identical to that described as above and an overlapped description thereof will be omitted.

The first vertically aligned polyimide may be a polymer compound represented by the following Chemical Formula 9, but is not limited thereto. In the Chemical Formula 9, a, b, c are each a natural number.

Chemical Formula 9

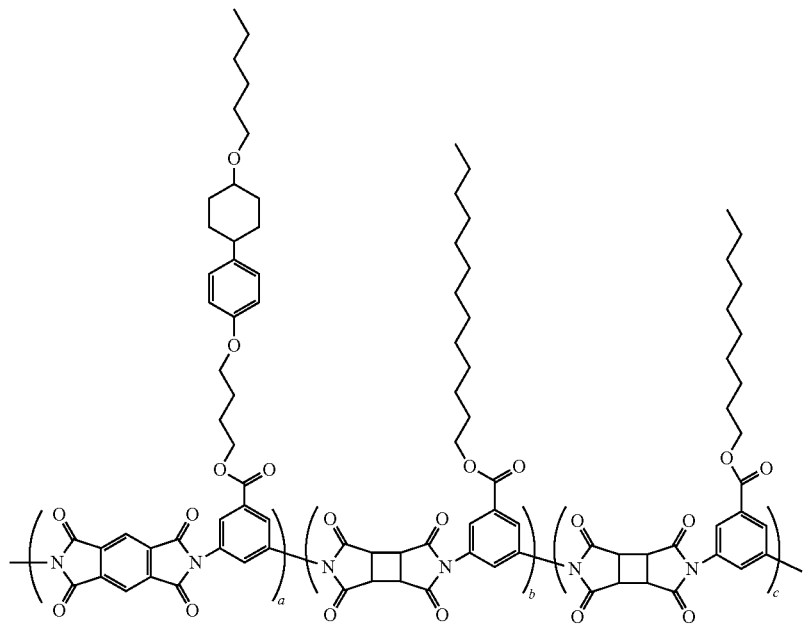

The pixel electrodes 291 may be disposed on the second flat substrate 200 and a 2-1$^{st}$ flat liquid crystal alignment layer AL2-1 may be disposed on the pixel electrodes 291.

The pixel electrodes 291 may be configured of one or more of an indium tin oxide, an indium zinc oxide, an indium oxide, a zinc oxide, a tin oxide, a gallium oxide, a titanium oxide, aluminum, silver, platinum, chromium, molybdenum, tantalum, niobium, zinc, magnesium, alloys thereof, and stack layers thereof. As described above, the pixel electrode 291 may be a pattern electrode having a slit pattern, and a portion of the second flat substrate 200 may be exposed through the slit pattern of the pixel electrode 291.

The 2-1$^{st}$ flat liquid crystal alignment layer AL2-1 may be formed of a polymer compound identical to the first vertically aligned polyimide of the first flat liquid crystal alignment layer ALL and may contain a reactive mesogen RM. That is, the 2-1$^{st}$ flat liquid crystal alignment layer AL2-1 is different from the first flat liquid crystal alignment layer AL1 in that it contains no light stabilizer.

The 2-1$^{st}$ flat liquid crystal alignment layer AL2-1 may be formed by, for example, applying a complex liquid crystal alignment agent containing a second vertically aligned polyimide having a vertical alignment group in a side chain thereof, and the reactive mesogen (RM), onto the pixel electrodes 291 and then, drying the same.

Figure 5:
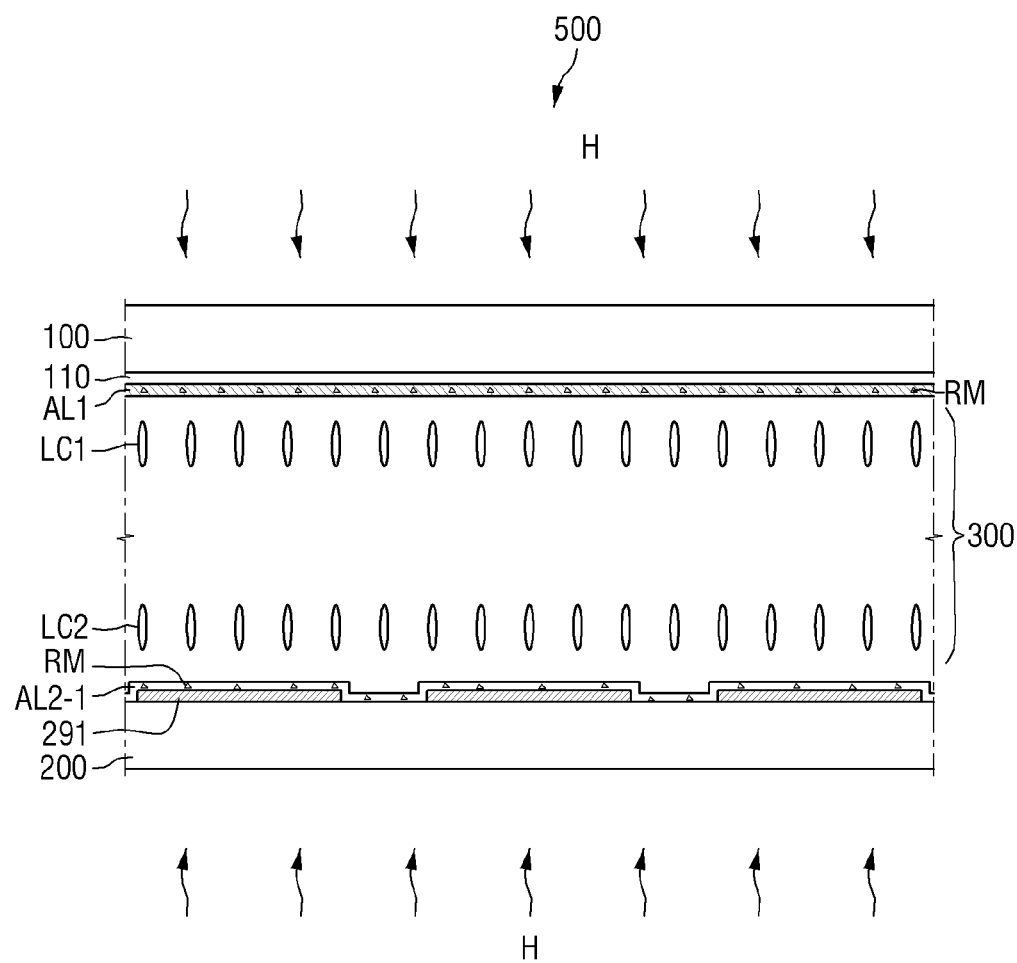

Referring to FIG. 5, a liquid crystal layer 300 may be disposed between the first flat substrate 100 and the second flat substrate 200 facing each other. The liquid crystal layer 300 may be formed by injecting or dropping a liquid crystal composition including liquid crystal molecules LC1 and LC2 into a space between the first flat substrate 100 and the second flat substrate 200.

Each of the liquid crystal molecules LC1 and LC2 may have negative dielectric constant anisotropy. In an initial state in which an electric field is not applied to a flat liquid crystal display 500, the liquid crystal molecules LC1 and LC2 may be aligned substantially vertically with respect to the first flat substrate 100 and the second flat substrate 200.

In other words, the respective vertical alignment groups of the first flat liquid crystal alignment layer AL1 and the 2-1$^{st}$ flat liquid crystal alignment layer AL2-1 may align the liquid crystal molecules LC1 and LC2 to be substantially vertically with respect to the first flat substrate 100 and the second flat substrate 200 in the initial state in which an electric field is not applied to the flat liquid crystal display 500. In this case, the term "being aligned substantially vertically" means that the liquid crystal molecules LC1 and LC2 are aligned in a range equal to or more than 87.5° and less than 90°, with respect to the first flat substrate 100 and the second flat substrate 200.

After the liquid crystal layer 300 is formed, a heat treatment H of applying heat to an upper portion or a lower portion of the first flat substrate 100 may be performed.

Figure 6:
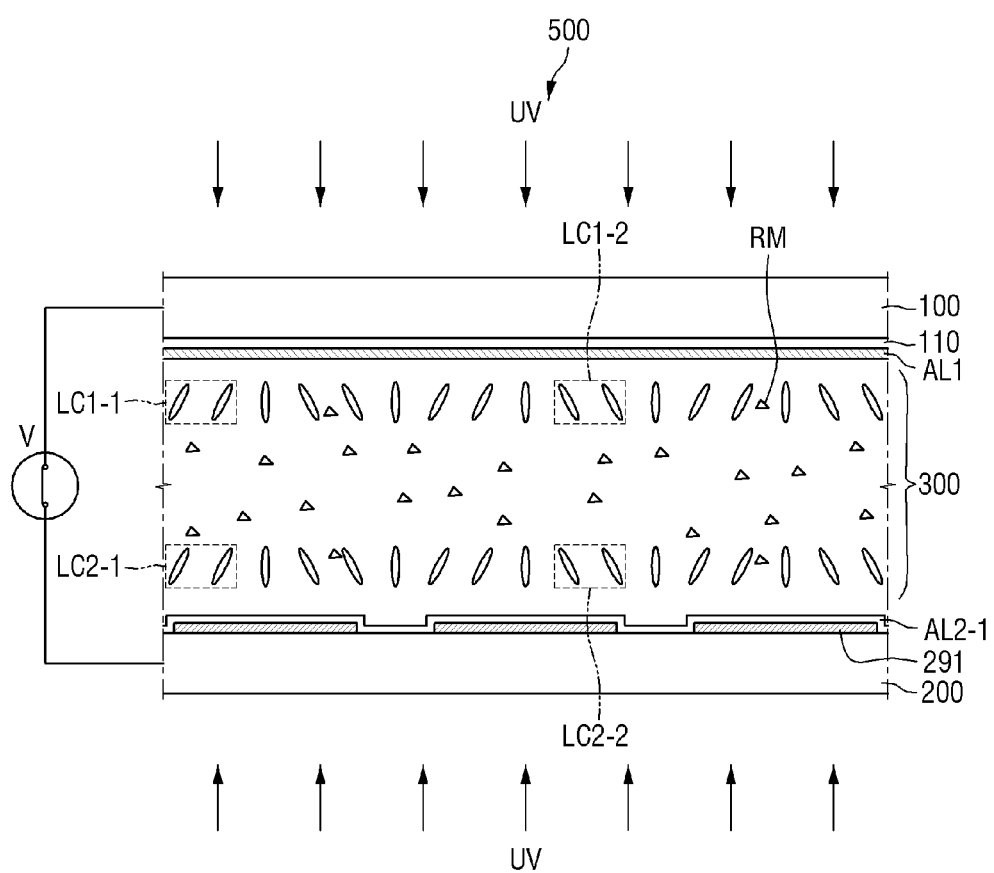

Referring to FIG. 6, through the heat treatment (H) illustrated in FIG. 5, the reactive mesogen RMs contained in the first flat liquid crystal alignment layer AL1 and the 2-1$^{st}$ flat liquid crystal alignment layer AL2-1 may be eluted to the liquid crystal layer 300.

When an electric field is applied to the flat liquid crystal display 500, liquid crystal molecules LC1-1, LC1-2, LC2-1, and LC2-2 are aligned at an incline in a direction perpendicular to an electrical field formed between the common electrode 110 and the pixel electrodes 291. That is, the 1-1$^{st}$ liquid crystal molecules LC1-1 and the 2-1$^{st}$ liquid crystal molecules LC2-1 may be aligned in a first inclination direction, and the 1-2$^{nd}$ liquid crystal molecules LC1-2 and the 2-2$^{nd}$ liquid crystal molecules LC2-2 may be aligned in a second inclination direction. Thereafter, when ultraviolet (UV) light is irradiated onto the flat liquid crystal display 500, photopolymerization of the reactive mesogen RM contained in the 2-1$^{st}$ flat liquid crystal alignment layer AL2-1 may be initiated to form a 2-2$^{nd}$ flat liquid crystal alignment layer AL2-2. On the other hand, since the first flat liquid crystal alignment layer AL1 contains the light stabilizer, the polymerization of the reactive mesogen RM may be inhibited.

Figure 7:
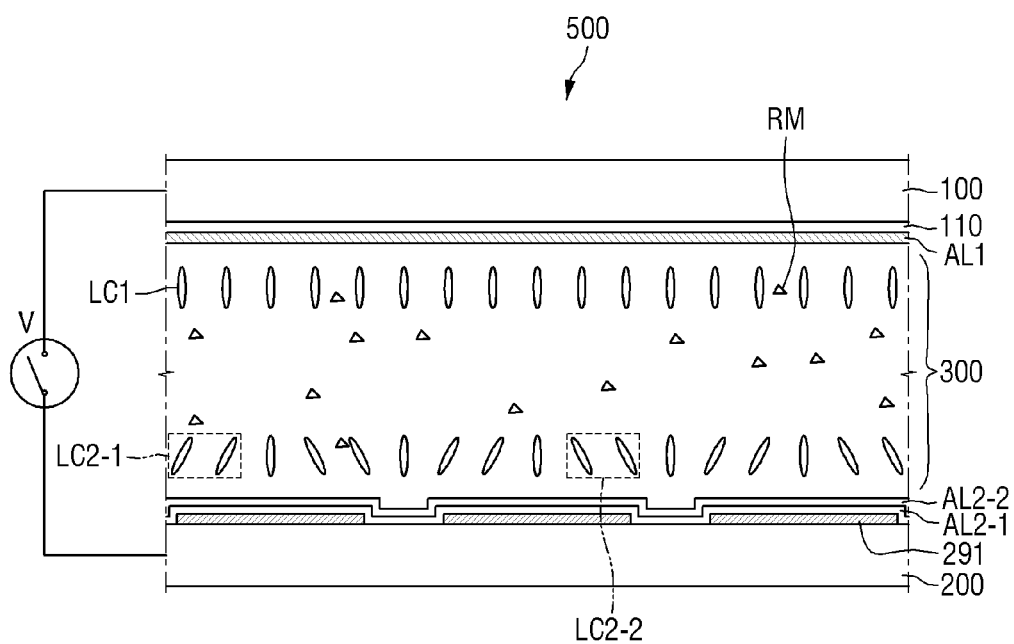

Referring to FIG. 7, the reactive mesogen RM may move toward the 2-1$^{st}$ flat liquid crystal alignment layer AL2-1 to form the 2-2$^{nd}$ flat liquid crystal alignment layer AL2-2. The 2-2$^{nd}$ flat liquid crystal alignment layer AL2-2 may be a polymer of reactive liquid crystal monomers and may be formed on the 2-1$^{st}$ flat liquid crystal alignment layer AL2-1. As the 2-2$^{nd}$ flat liquid crystal alignment layer AL2-2 is formed, the amount of the reactive mesogen RM in the liquid crystal layer 300 may be gradually decreased. The reactive mesogen RM may be understood as being used in forming the 2-2$^{nd}$ flat liquid crystal alignment layer AL2-2 thereby decreasing the amount of reactive mesogen.

The 2-2$^{nd}$ flat liquid crystal alignment layer AL2-2 may fix or stabilize the alignment directions of the second liquid crystal molecules LC2-1 and LC2-2. Therefore, even in the case where the electric field applied to the flat liquid crystal display 500 is released, the inclined alignment of the second liquid crystal molecules LC2-1 and LC2-2 arranged on the surface of the 2-2$^{nd}$ flat liquid crystal alignment layer AL2-2 may be maintained. On the other hand, when the electric field applied to the flat liquid crystal display 500 is released, the first liquid crystal molecules LC1 may be substantially vertically aligned, similar to the initial state in which the electric field is not applied.

Figure 8:
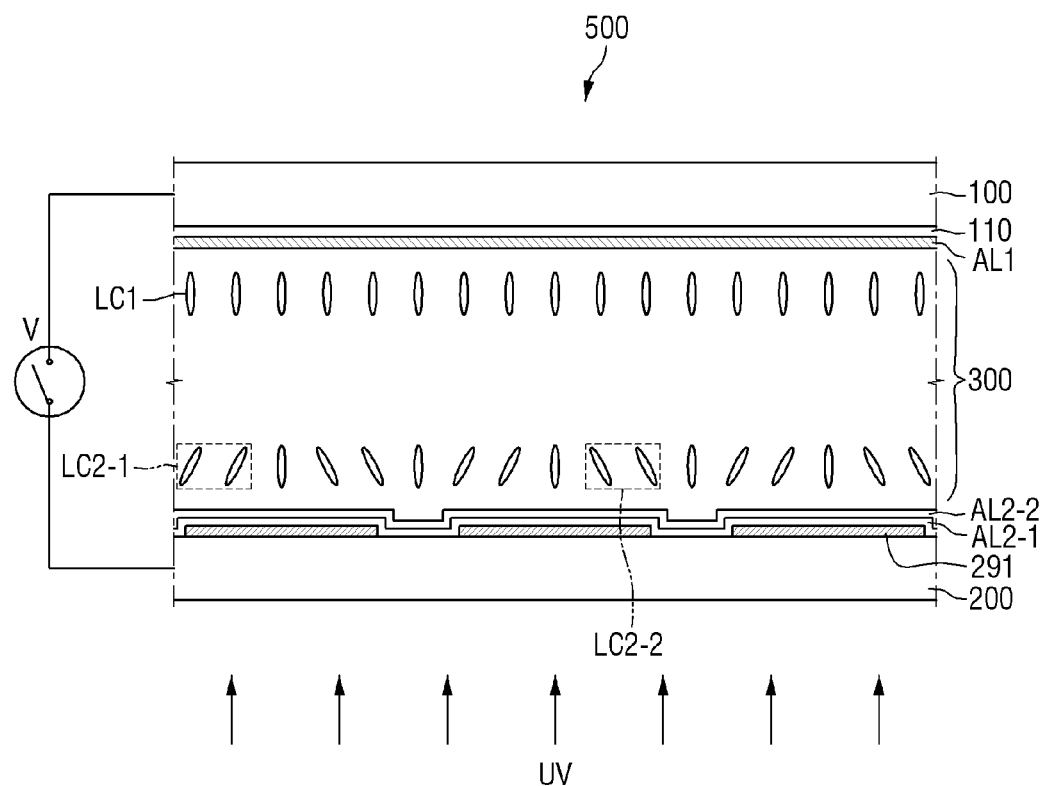
Figure 9:
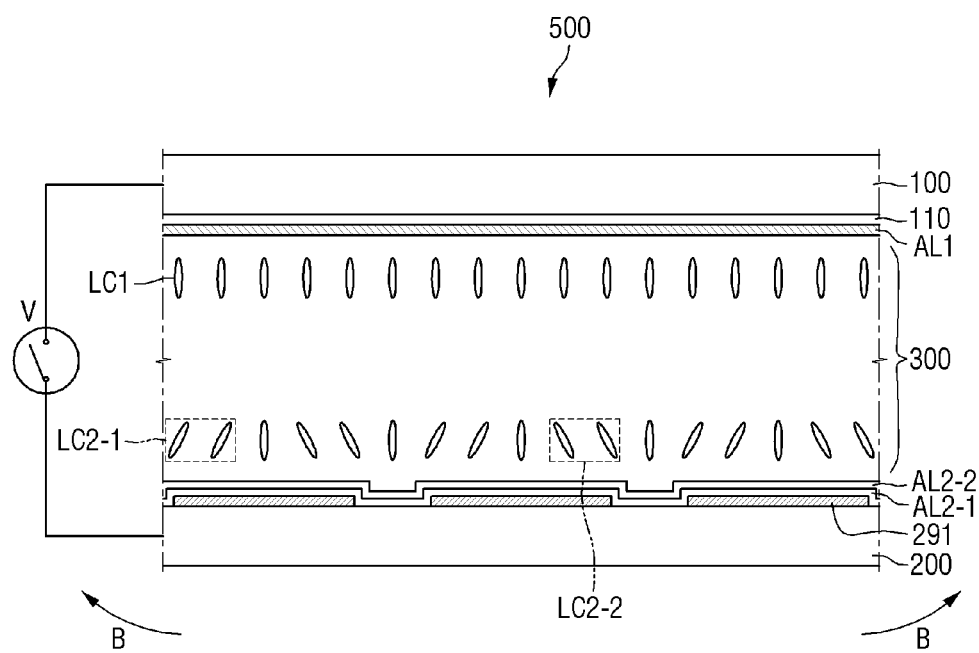

Referring to FIG. 8 and FIG. 9, in the state in which the electric field is not applied to the flat liquid crystal display 500, residual reactive mesogen RM may be removed by irradiating fluorescent UV light onto the flat liquid crystal display 500. Thereafter, the curved liquid crystal display 500C of FIG. 3 may be manufactured through a bending process B in order to bend both ends of the flat liquid crystal display 500.

Figure 10:
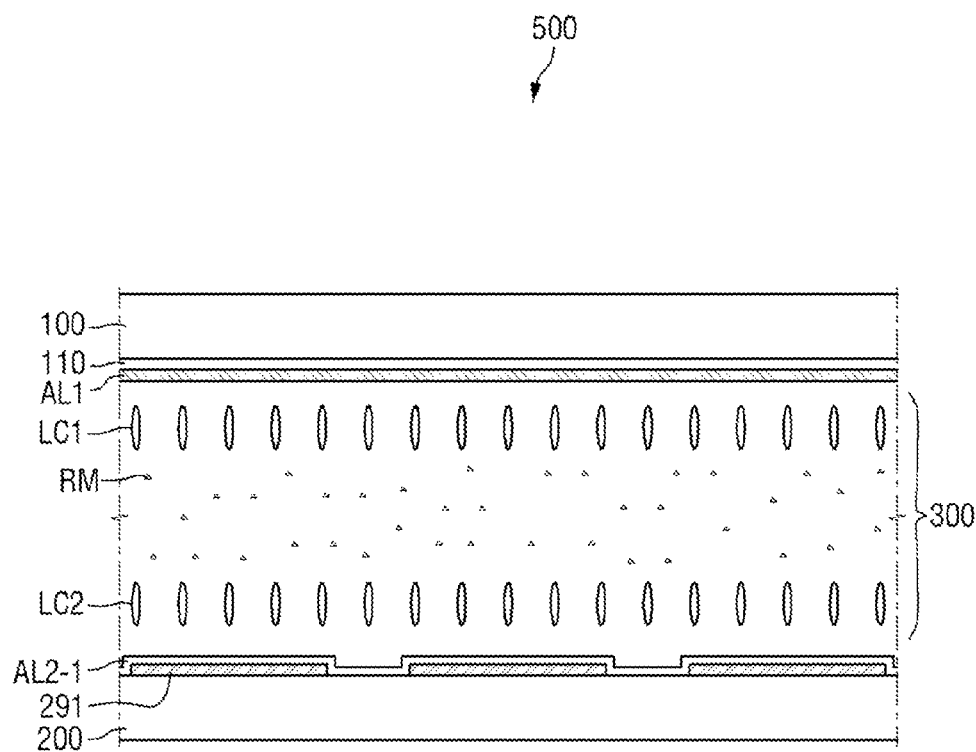
FIG. 10 is a cross-sectional view illustrating another exemplary embodiment of a method of manufacturing a curved liquid crystal display.

Alternatively, the reactive mesogen RM may be contained in the liquid crystal layer 300. That is, as shown in FIG. 10, the first flat liquid crystal alignment layer AL1 may contain the first vertically aligned polyimide having the vertical alignment group present as a side chain thereof, and the light stabilizer, but may not contain the reactive mesogen. The 2-1$^{st}$ flat liquid crystal alignment layer AL2-1 may contain the first vertically aligned polyimide having the vertical alignment group present as a side chain thereof, but may not contain the reactive mesogen. The reactive mesogen (RM) may be present in a state in which it is mixed with liquid crystal elements within the liquid crystal layer 300.

Figure 11:
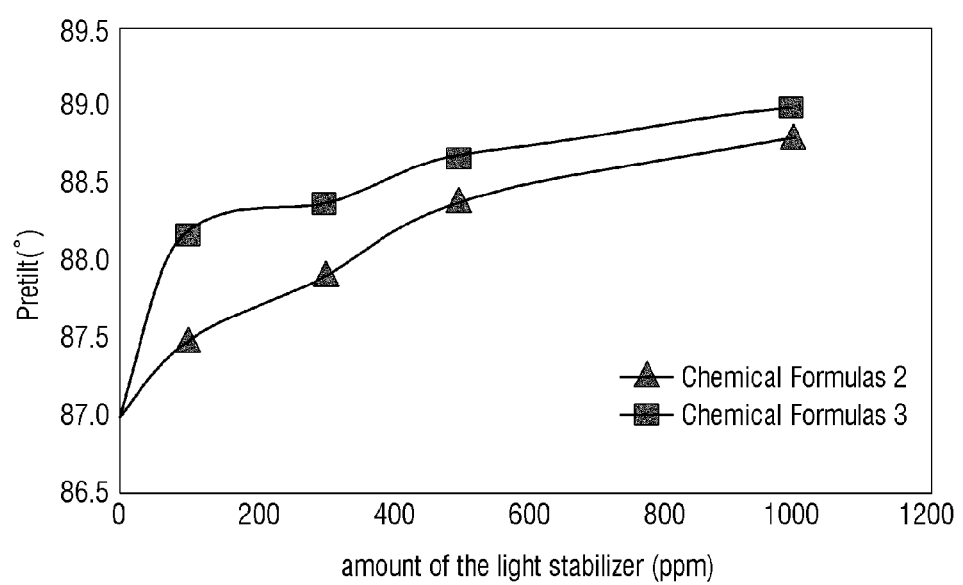
FIG. 11 is a graph illustrating the pretilt angles versus the content of light stabilizer contained in an alignment layer.

Meanwhile, FIG. 11 is a graph illustrating the pretilt angles versus the amount of the light stabilizer in the case where the light stabilizer is present in an alignment layer. The graph was prepared by measuring the pretilt angles of liquid crystals manufactured when the light stabilizer is not contained in an alignment layer (0 ppm) and when the light stabilizer is contained in the alignment layer. In the graph of FIG. 11, the horizontal axis refers to the amount (ppm) of the light stabilizer and a vertical axis refers to a pretilt angle)(°. Variations in the pretilt angle were measured by inputting respective amounts of the components according to Chemical Formulas 2 and 3.

As shown in FIG. 11, it could be confirmed that as the input amount of the light stabilizer of Chemical Formula 2 and 3 was increased, the alignment of the liquid crystals was closer to a vertical alignment. That is, it could be confirmed that as the amount of the light stabilizer was increased, the polymerization of reactive mesogen was inhibited and prevented the alignment of the liquid crystals from being fixed. This was true even in the case of irradiating UV light at the same time in which an electric field is applied, thereby allowing the liquid crystals to be aligned closely to the vertical alignment.

In the graph of FIG. 11, the case of 0 ppm, refers to a case in which the light stabilizer is not contained within an alignment layer. The case may correspond to the 2-1$^{st}$ flat liquid crystal alignment layer AL2-1 in FIG. 5. It could be confirmed that a pretilt angle in the case of 0 ppm light stabilizer was 87°. On the other hand, the case in which the light stabilizer is partially present may correspond to the first flat liquid crystal alignment layer AL1 in FIG. 5. In this case, it could be confirmed that the pretilt angle ranged between 87.5° and 89°, such that the alignment of the liquid crystals was closer to the vertical alignment as compared to the case of 0 ppm.

As in the data of FIG. 11, in exemplary embodiments, the light stabilizer may be included in one alignment layer on one side of a pair of alignment layers facing each other, while the light stabilizer may not be included in the opposite alignment layer. As a result, liquid crystals adjacent to the one side including the light stabilizer are only vertically aligned to thereby prevent the recognition (visibility) of the texture occurring due to the collision of alignment directions of liquid crystal molecules While exemplary embodiments of the present invention have been shown and described above, it will be apparent to those skilled in the art that modifications and variations could be made without departing from the spirit and scope of the present invention as defined by the appended claims.

As set forth above, according to the exemplary embodiments, the curved liquid crystal display can have improved light transmissivity.

In addition, the occurrence of unnecessary patterns or spots due to the application of a curved panel may be prevented.

Effects according the present invention are not limited to the contents exemplified above and more various effects are involved in the specification.

What is claimed is:
1. A curved liquid crystal display comprising:
a first curved substrate;
a second curved substrate facing the first curved substrate;
a liquid crystal layer disposed between the first curved substrate and the second curved substrate;
a first curved liquid crystal alignment layer disposed between the liquid crystal layer and the first curved substrate and containing a light stabilizer; and
a second curved liquid crystal alignment layer disposed between the liquid crystal layer and the second curved substrate,
wherein the light stabilizer is a compound represented by following Chemical Formula 1:

Chemical Formula 1

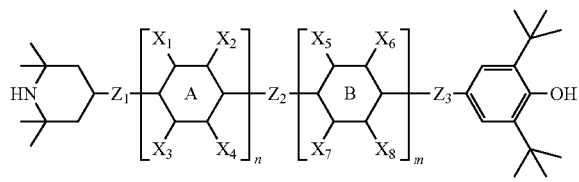

wherein, n is 0 or 1; m is 0 or 1; Z1 to Z3 are each independently a single bond, a divalent alkenyl group, a divalent alkyl group, a divalent alkoxy group, —C(O)O—, or —CF$_2$O—; X1 to X8 are each independently an alkyl group, H, F, or CF$_3$; and A and B are each independently of the following formulas:

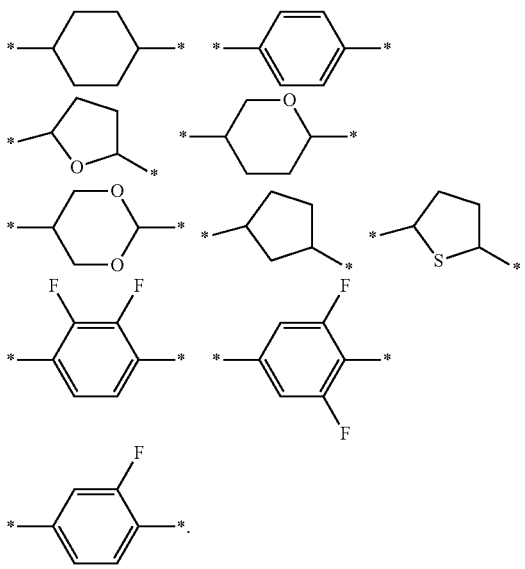

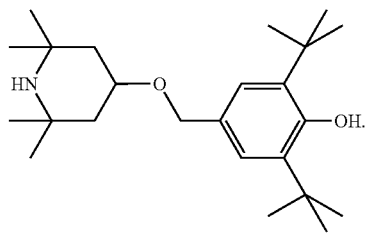

Chemical Formula 3

2. The curved liquid crystal display of claim 1, wherein the second curved liquid crystal alignment layer does not contain the light stabilizer.

3. The curved liquid crystal display of claim 2, wherein the second curved liquid crystal alignment layer comprises a reactive mesogen and an amount of the reactive mesogen is higher in the second curved liquid crystal alignment layer than an amount in the first curved liquid crystal alignment layer.

4. The curved liquid crystal display of claim 2, wherein the second curved liquid crystal alignment layer has a multilayer structure including a 2-$1^{st}$ curved liquid crystal alignment layer and a 2-$2^{nd}$ curved liquid crystal alignment layer comprising a reactive mesogen, and an amount of the reactive mesogen in the 2-$2^{nd}$ curved liquid crystal alignment layer is higher than an amount in the 2-$1^{st}$ curved liquid crystal alignment layer.

5. The curved liquid crystal display of claim 1, wherein in the Chemical Formula 1, Z1 to Z3 are each independently a single bond, a divalent alkenyl group having 2 to 5 carbon atoms, a divalent alkyl group having 1 to 5 carbon atoms, a divalent alkoxy group, —C(O)O—, or —CF$_2$O—; and X1 to X8 are each independently CH$_3$, H, F, or CF$_3$.

6. The curved liquid crystal display of claim 1, wherein the light stabilizer is represented by the following Chemical Formula 2:

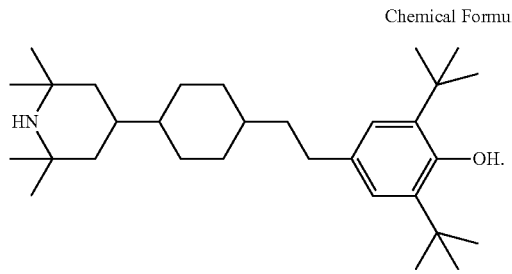

Chemical Formula 2

7. The curved liquid crystal display of claim 1, wherein the light stabilizer is represented by following Chemical Formula 3:

8. The curved liquid crystal display of claim 1, wherein the light stabilizer is in a derivatized form and is present as a side chain of a polyimide in the first curved liquid crystal alignment layer.

9. The curved liquid crystal display of claim 1, wherein the light stabilizer is present in an amount of greater than 0 ppm and equal to or less than about 10,000 ppm with respect to an overall weight of the first curved liquid crystal alignment layer.

10. The curved liquid crystal display of claim 1, wherein the liquid crystal layer includes first liquid crystal molecules having negative dielectric constant anisotropy aligned with a surface of the first curved liquid crystal alignment layer, and second liquid crystal molecules aligned with a surface of the second curved liquid crystal alignment layer, and wherein the first liquid crystal molecules are vertically aligned as compared to the second liquid crystal molecules when an electrical field is not applied to the liquid crystal layer.

11. The curved liquid crystal display of claim 1, further comprising:

a patternless electrode disposed between the first curved substrate and the first curved liquid crystal alignment layer and having no slit pattern; and a pattern electrode disposed between the second curved liquid crystal alignment layer and the second curved substrate and having a slit pattern.

12. A method of manufacturing a curved liquid crystal display, comprising:

preparing a first curved substrate and a second curved substrate facing each other;

forming a first curved liquid crystal alignment layer on a surface of the first curved substrate facing the second curved substrate;

forming a second curved liquid crystal alignment layer on a surface of the second curved substrate facing the first curved substrate;

injecting a liquid crystal composition into a space between the first curved substrate and the second curved substrate; and irradiating ultraviolet light in a direction toward at least one of the first curved substrate and the second curved substrate when an electric field is applied, wherein the first curved liquid crystal alignment layer comprises a light stabilizer, wherein the light stabilizer is a compound represented by following Chemical Formula 1:

Chemical Formula 1

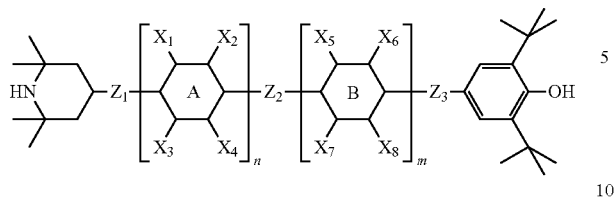

wherein, n is 0 or 1; m is 0 or 1; Z1 to Z3 are each independently a single bond, a divalent alkenyl group, a divalent alkyl group, a divalent alkoxy group, —C(O)O—, or —CF$_2$O—; X1 to X8 are each independently an alkyl group, H, F, or CF$_3$; and A and B are each independently of the following formulas:

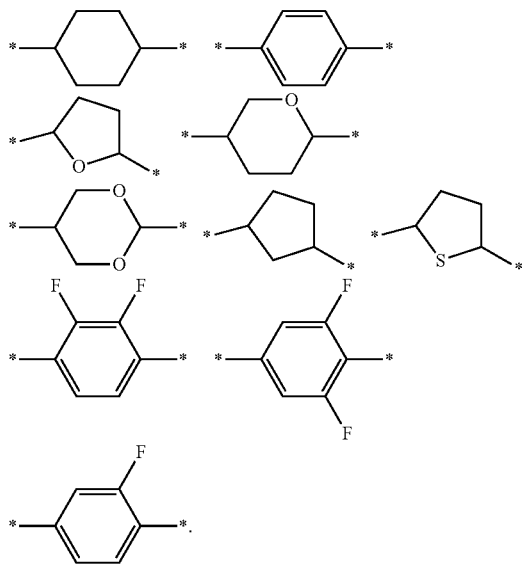

13. The method of claim 12, wherein in Chemical Formula 1, Z1 to Z3 are each independently a single bond, a divalent alkenyl group having 2 to 5 carbon atoms, an alkyl group having 1 to 5 carbon atoms, an alkoxy group, —C(O)O—, or —CF$_2$O—; and X1 to X8 are each independently CH$_3$, H, F, or CF$_3$.

14. The method of claim 12, wherein the light stabilizer is represented by following Chemical Formula 2:

Chemical Formula 2

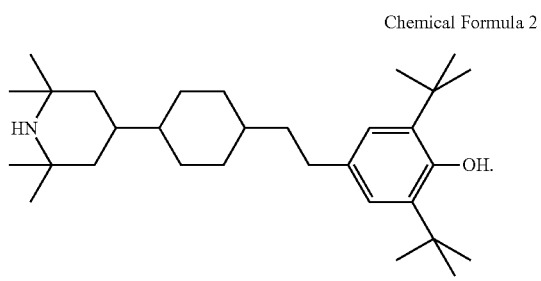 [SMILES: CC1(C)CC(C2CCC(CCc3cc(C(C)(C)C)c(O)c(C(C)(C)C)c3)CC2)CC(C)(C)N1]

15. The method of claim 12, wherein the light stabilizer is represented by following Chemical Formula 3:

Chemical Formula 3

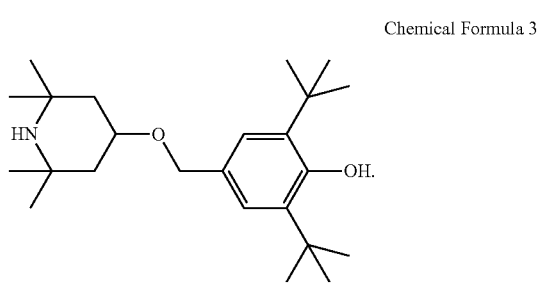 [SMILES: CC1(C)CC(OCc2cc(C(C)(C)C)c(O)c(C(C)(C)C)c2)CC(C)(C)N1]

16. The method of claim 12, wherein the light stabilizer is present in an amount of greater than 0 ppm and equal to or less than about 10,000 ppm with respect to an overall weight of the first curved liquid crystal alignment layer.

17. The method of claim 12, wherein at least one of the first curved liquid crystal alignment layer, the second curved liquid crystal alignment layer, and the liquid crystal composition comprises a reactive mesogen.

18. The method of claim 17, wherein due to the irradiating of ultraviolet light, the second curved liquid crystal alignment layer has a multilayer structure comprising a 2-1$^{st}$ curved liquid crystal alignment layer and a 2-2$^{nd}$ curved liquid crystal alignment layer, and an amount of reactive mesogen in the 2-2$^{nd}$ curved liquid crystal alignment layer is higher than an amount in the 2-1$^{st}$ curved liquid crystal alignment layer.

* * * * *